(12) United States Patent
Olsen et al.

(10) Patent No.: US 8,319,003 B2
(45) Date of Patent: Nov. 27, 2012

(54) ADHESIVE WAFER

(75) Inventors: Hans Olsen, Hoersholm (DK); Jakob Oeelund, Alleroed (DK); Danuta Ciok, Nivaa (DK)

(73) Assignee: Coloplast A/S, Humlebaek (DK)

( * ) Notice: Subject to any disclaimer, the term of this patent is extended or adjusted under 35 U.S.C. 154(b) by 742 days.

(21) Appl. No.: 12/226,722

(22) PCT Filed: Apr. 19, 2007

(86) PCT No.: PCT/DK2007/000184
§ 371 (c)(1),
(2), (4) Date: Mar. 5, 2009

(87) PCT Pub. No.: WO2007/121744
PCT Pub. Date: Nov. 1, 2007

(65) Prior Publication Data
US 2009/0312685 A1  Dec. 17, 2009

(30) Foreign Application Priority Data

Apr. 25, 2006 (DK) .................................. 2006 00604

(51) Int. Cl.
*A61F 15/00* (2006.01)
(52) U.S. Cl. ............ 602/54; 602/46; 604/332; 604/336; 604/338; 604/339
(58) Field of Classification Search .................... 602/54, 602/42, 43, 52, 55, 57, 58; 604/307, 308, 604/304, 305, 332, 337, 338, 342, 344; 424/447, 424/448, 449
See application file for complete search history.

(56) References Cited

U.S. PATENT DOCUMENTS

| | | | | | |
|---|---|---|---|---|---|
| 2,349,709 | A | * | 5/1944 | Evans | 428/196 |
| 4,367,732 | A | | 1/1983 | Poulsen et al. | |
| 4,457,754 | A | * | 7/1984 | Buttaravoli | 604/180 |
| 4,551,490 | A | | 11/1985 | Doyle et al. | |
| 5,013,307 | A | * | 5/1991 | Broida | 604/338 |
| 5,051,259 | A | * | 9/1991 | Olsen et al. | 424/443 |
| 5,123,900 | A | * | 6/1992 | Wick | 602/41 |
| 5,395,675 | A | * | 3/1995 | Altholz et al. | 428/195.1 |
| 5,486,158 | A | * | 1/1996 | Samuelsen | 602/46 |
| 5,865,819 | A | * | 2/1999 | Cisko et al. | 604/339 |
| 6,589,222 | B1 | * | 7/2003 | Olsen | 604/336 |
| 2002/0165477 | A1 | * | 11/2002 | Dunshee | 602/58 |
| 2004/0260256 | A1 | * | 12/2004 | Ciok et al. | 604/332 |

FOREIGN PATENT DOCUMENTS

| | | |
|---|---|---|
| DK | 147035 B | 6/1982 |
| EP | 0 591 440 B1 | 4/1994 |
| EP | 768071 A1 | 4/1997 |
| EP | 0 806 210 A2 | 11/1997 |

(Continued)

*Primary Examiner* — Patricia Bianco
*Assistant Examiner* — Caitlin Carreiro
(74) *Attorney, Agent, or Firm* — Coloplast A/S; Daniel G. Chapik; Nicholas R. Baumann (57) ABSTRACT

An adhesive wafer for an ostomy faceplate or wound dressing comprising a backing layer, said backing layer having one surface facing the skin, said surface comprising a first and a second adhesive zone being separated from each others by a void volume, said void volume being defined by the backing layer, the first and the second adhesive zones and the skin surface and wherein the first and the second adhesive zones are capable of moving independently of each others with respect to the lateral plane of the backing layer.

18 Claims, 7 Drawing Sheets

FOREIGN PATENT DOCUMENTS

| | | | |
|---|---|---|---|
| EP | 806210 A2 * | 11/1997 |
| EP | 0 898 471 B1 | 3/1999 |
| EP | 1699052 A1 * | 9/2006 |
| GB | 2 283 916 A | 5/1995 |
| GB | 2283916 A * | 5/1995 |
| JP | 2004535212 | 11/2004 |
| WO | WO 93/00056 | 1/1993 |
| WO | WO 94/15562 | 7/1994 |
| WO | WO 9415562 A1 * | 7/1994 |
| WO | WO 97/42917 | 11/1997 |
| WO | WO 98/17212 | 4/1998 |
| WO | WO 2004087004 | 10/2004 |

\* cited by examiner

ADHESIVE WAFER

This is a national stage of PCT/DK07/000184 filed Apr. 19, 2007 and published in English, which has a priority of Denmark no. PA 2006 00604 filed Apr. 25, 2006, hereby incorporated by reference.

FIELD OF THE INVENTION

The present invention refers to a skin-friendly adhesive wafer for covering wounds, burns or similar damages of the human skin, or ostomy openings.

BACKGROUND OF THE INVENTION

Adhesive wafers for ostomy appliances or wound dressings are usually in the form of a backing layer coated on the skin-facing surface with an adhesive layer. Even if both the adhesive and the backing layer are soft and flexible, the skin surface onto which the wafer is applied will move dependent on the wafers movements, a movement at the edge of the wafer may cause a stress transmitting through the entire wafer. This may cause discomfort and trauma to the skin and build up tension in the wafer, leading to loosening of its tack and increasing the risk of leakage. In an ostomy appliance the wafer typically carries a collecting bag, said bag may also induce pulling and dragging forces to the wafer. Such forces induced in the wafer are often lateral, i.e. parallel to the wafer, and the known wafers are not very flexible with respect to lateral movements.

From European patent No. 768 071 is known a wound dressing comprising a hydrocolloid containing adhesive layer, a flexible backing film secured to the non-skin contacting side of the adhesive layer, said backing film having at least one linear depression, the thickness of the adhesive in the depression being less than the thickness of the adhesive layer alongside the depression. The adhesive layer is continuously covering the backing film, and provides a continuous adhesive surface against the skin, but the layer of adhesive is thinner in the depressions than in the surrounding parts. These depressions make the dressing more flexible and easier to bend when applied to curved surfaces, e.g. sacrum.

European patent No. 591 440 discloses a wound dressing, preferably of the hydrocolloid type, in which is made grooves or ditches that fully or partly surrounds a central part of the adhesive sheet. The grooves and ditches are arranged concentric or radially outwardly from the central part and have a depth so that the thickness of the sheet at the bottom of the ditch is less than ¼ of the thickness of the sheet between the ditches. The ditches and grooves facilitate a higher flexibility of the dressing with respect to bending as well as they can work as a stop point to the absorbed fluid.

The ostomy appliances disclosed in both European patent No. 591 440 and European patent No. 768 071 both suffer from the drawback that even though the depressions/grooves in the dressings add greater flexibility to the dressing, this flexibility is only in the bending and curving process. European patent No. 591 440 and European patent No. 768 071 do not teach or indicate lateral flexibility to allow sideward stretching of an ostomy appliance, or individual movement of select parts of the dressing. Such separate movements are not possible for the embodiments shown in European patent No. 591 440 and European patent No. 768 071.

From European patent No. 898 471 is known a wound dressing comprising a backing layer, an absorbent layer and a skin-contacting layer. The dressing is provided with one or more seals circumscribing the central portion. The seals are made by applying ultrasonic or thermal energy thus creating a groove from the skin surface to the backing layer, the sides of said groove being covered with a water-impervious material, e.g. adhesive. The seals serve as barriers for leakage. The reference is silent with respect to the ability of lateral movement.

It has surprisingly been found that it is possible to provide an adhesive wafer having lateral flexibility offering a convenient and comfortable solution to the above problems.

BRIEF DESCRIPTION OF THE INVENTION

One object of the present invention is to provide an adhesive wafer having an enhanced flexibility, especially in lateral direction.

Another object of the invention is to provide a leakage proof wafer.

Yet another object of the invention is to provide a wafer comprising two or more different adhesives.

BRIEF DESCRIPTION OF THE DRAWINGS

The invention is explained more in detail with reference to the drawings in which.

DETAILED DESCRIPTION OF THE INVENTION

The invention relates to an adhesive wafer for an ostomy faceplate or wound dressing comprising a backing layer, said backing layer having one surface facing the skin, said surface comprising a first and a second adhesive zone being separated from each other by a void volume, said void volume being defined by the backing layer and the first and the second adhesive zones and the skin surface, and wherein the first and the second adhesive zone are capable of moving independently of each other with respect to the plane of the backing layer.

The void volume may be in the form of a canal, preventing direct contact between the two adhesive zones. The void volume may serve as a buffer for the movements of the two adhesive zones with respect to each other. A bridge of the backing layer, the backing layer being the "roof" of the canal, connects the two adhesive zones to each other. "Void volume" means a cavity or hollow space and is distinct from wafers with grooves.

The backing film of the void volume is preferably not in contact with the skin, thus creating a three-dimensional void volume. The volume may also serve as a leakage barrier, stopping any fluid leakage from progressing from the centre of the wafer and towards the edge. The leaking fluid will be trapped and distributed in the void volume, thus reducing or eliminating the pressure on the outer adhesive zone. Thus the volume may serve as a reservoir for leaking fluid. If the backing layer is transparent or translucent, the leakage may be visible from the non-skin-facing surface of the wafer, thus indicating to the user that it is time for changing the wafer.

It is preferred that the backing layer of the void volume is non-adhesive in order to prevent it from adhering to itself, the skin or other parts of the wafer, thus reducing the mobility of the adhesive zones.

For further enhancing the flexibility of the wafer, the backing layer of the void volume may be deformed, e.g. by stretching, in order to produce a surplus of backing layer over the void volume. Such surplus of backing layer will facilitate movement of the adhesive zones substantially independent of the backing layer.

In one embodiment of the invention the backing layer of the void volume is plied, thus providing an excess of backing layer for free movement. The layer may e.g. be plied like an accordion or in a lateral pleat.

It is preferred that the adhesive zones are in the form of annular structures, e.g. concentric circles, squares or other geometric figures as well as the wafer itself may have different configurations such as circle, ellipse or other suitable shape. The first and the second adhesive zones are preferably concentric. The centre of the zones may be the central portion of the wafer or the centre may be asymmetric, i.e. such that the width of the adhesive zone may be larger on one side of the wafer than on the other. By having the void volume as a closed ring structure, the risk of leakage escaping from the volume is reduced, and the effect as leakage barrier is enhanced.

The presence of the void volume renders it possible to employ two or more different adhesives on the same application, event though the adhesive may not be compatible. In one embodiment of the invention the first and the second adhesive zones comprise different adhesives. It may be desired to have one type adhesive, e.g. an absorbent adhesive, at the central adhesive zone, and another, less absorbent, but more tacky, at the peripheral portion of the wafer.

In one embodiment of the invention the wafer comprises a coupling ring or a collecting bag. The embodiment may be especially suitable for ostomy appliances, comprising a coupling ring for attaching a collecting bag (two-piece system) or the bag may be directly attached to the wafer (one-piece system). The coupling ring may be an adhesive coupling, or a traditional coupling ring.

In another embodiment of the invention the wafer comprises an absorbent pad. This embodiment may be e.g. suitable for use as a wound dressing.

The adhesive wafer of the present invention may comprise three or more adhesive zones. A plurality of adhesive zones separated by canals may facilitate maximum flexibility and provide an effective guard against leakage. However, the more adhesive zones, the less adhesive surface for attachment to the skin. In order to ensure safe attachment to the skin, two adhesive zones may usually be sufficient. A wound dressing for application to body parts where high flexibility is demanded, e.g. joints, may preferably contain more than two adhesive zones.

In one embodiment of the invention the void volume comprises foam. The foam may act as a spacer, keeping the adhesive zones from direct contact, and it may help distribute any leakage fluid in the volume, so it does not build up a pressure against the second adhesive for further leakage. The foam is preferably soft and easily compressible in order not to interfere with the flexibility of the wafer. The foam may be any suitable foam such as polymer foam. The foam may be absorbent or non-absorbent.

The backing layer of the wafer of the invention is preferably in the form of a flexible film. The film may be elastic and/or stretchable/easily deformable. Examples of suitable material for such backing layer may be polyethylene, polypropylene, polyurethane, polyvinyl chloride or laminates of these. The film is flexible in order to facilitate the individual movements of the adhesive zones. It may be elastic, thus easily stretchable, but returns to it original shape, or it may be plastic, thus being permanently deformed when stretched.

The lateral width of the void volume may be 1-20 mm, more preferred 1-15 mm, even more preferred 2-10 mm and most preferred 3-8 mm. By the lateral width is meant the distance, in the plane of the backing layer, from the edge of the first adhesive zone to the edge of the second adhesive zone. The optimal distance is dependent on several parameters, the desired flexibility, the choice of material, especially for the backing layer, the thickness of the adhesive zones, the use of the wafer (ostomy wafer or wound dressing), the deformation of the backing layer, etc.

The thickness of the adhesive layer may preferably be 0.1-2 mm more preferred 0.7-1.5 mm. Wafers for ostomy appliances comprise often a relatively thick adhesive layer, e.g. 0.8-1.5 mm, while wound dressing may be thinner. In one embodiment of the invention the adhesive zones may have different thickness. The wafer of the invention may comprise a central portion, e.g. the first adhesive zone, and an outer portion, e.g. the second adhesive zone, encircling the central portion. The central portion may have a diameter of 40-80 mm, more preferred 50-75 mm and the outer portion may have a diameter of 80-130, more preferred 90-120 mm.

In one embodiment of the invention the central adhesive zone may vary in thickness, e.g. having a thickness up to 1 cm at the part surrounding the central aperture for the stoma, then decreasing in thickness radially towards the void volume to a thickness of 0.2-0.7 cm.

In one embodiment of the invention the edge portion of the adhesive layer facing the void volume is provided with a non-adhesive layer. The layer facilitates that the edge portions of the adhesive does not adhere to each other when the zones are moved laterally. The non-adhesive layer is in the form of a coating, such as silicone or a powder for reducing the adhesive tack of the edge portion.

In another embodiment of the invention the non-adhesive layer is in the form of a polymer film. The film may be in the form of strips covering the edge portions of the adhesive and optionally bending around the corner of the adhesive zone, thus covering the edge of the skin-facing surface of the adhesive. The strip may be one strip, extending from one edge portion over the backing layer of the void volume and including the other edge portion, or it may be two strips, covering each edge portion, but not the backing layer. The strip may be prepared from any suitable material, but preferably from the same material as the backing layer.

Figure 9:
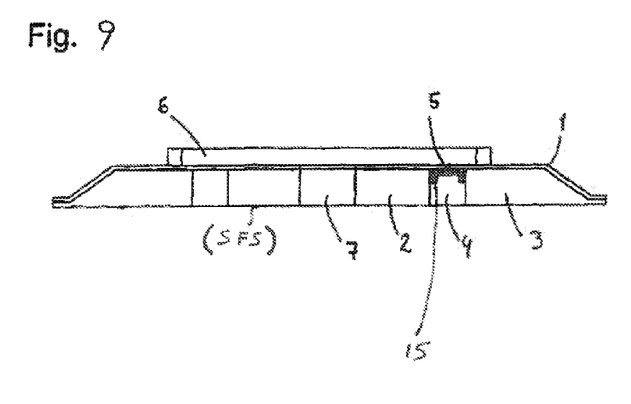
FIG. 9 is a simplified cross-sectional view of one embodiment of an adhesive wafer.

The void volume may be provided with moisture indicator means 15 (FIG. 9). Such indicator means may e.g. be in the form of a colour indicator producing a change of colour when exposed to moisture. Thus it will be easy for the user or care personnel to see that it is time for changing the wafer.

Deforming or stretching the backing layer may achieve lateral flex. This may be done in different ways: The backing layer may be laminated to the adhesive zones, and afterwards the layer is stretched to deformation. The layer will only be deformed in the zone not being covered with adhesive as the adhesive may provide the other zones with a certain stability and rigidity. Dragging or pulling the inner zone deforms the layer.

Alternatively, the film may be thermoformed by introducing heat and pressure. Placing the wafer in a mould and introducing vacuum or introducing a tool, thus deforming the layer, may do this.

In a preferred embodiment the adhesive wafer is an ostomy faceplate with a coupling ring for a collection bag. The first adhesive zone is in the form of a disc surrounding the stoma aperture, said disc having a diameter less than or the same as the coupling ring, the second adhesive zone may be oriented concentric around the first disc, separated from this by the void volume, the second zone preferably carrying a coupling for an ostomy pouch, or carrying the ostomy pouch directly. The first adhesive zone may be a non-memory, putty-like adhesive, which renders it possible to pack the adhesive fluid-tight around the stomal aperture, while the second adhesive area comprises an adhesive with a good tack, but less absorbent. The void volume between the adhesive zones provides a larger mobility of the inner adhesive zone around the stoma aperture, without focussing the stress to the whole of the wafer. Furthermore, there is no interference between the two types of adhesive as the void volume physically separates them.

The central adhesive zone may e.g. comprise putty-like adhesive as disclosed in WO 98/17212 and the second peripheral zone may comprise any suitable skin-friendly adhesive, e.g. those disclosed in U.S. Pat. No. 4,551,490 and DK 147 035. Other suitable adhesives for the second zone may e.g. be silicone or polyurethane containing adhesives.

The void volume renders it possible for the dressing to follow the movements of the skin and to cover irregular areas of the skin. The adhesive zones obtain more mobility compared to each other when they are separated with a void volume.

A conventional dressing or ostomy wafer usually comprises a continuous surface of adhesive towards the skin. When the covered area of the skin is exposed to moving forces, the skin under the plate will act as one relatively stiff plate, causing all of the pulling forces to be concentrated in the skin right next to the dressing. This may cause severe stress to this part of the skin and also add stress to the rim of the dressing, causing it to loosen the grip and slipping off.

By dividing the adhesive surface into a plurality of discrete adhesive areas, the force across the wafer will also be divided, as well as only the part of the wafer exposed to the movement will be affected.

The broader the void volume of the wafer is, the more independently the adhesive zones are able to move. If the backing layer of the void volume furthermore is deformed, this will provide even more flexibility, which is important especially around the stoma. Here movements in the skin around the stoma will, in a traditional wafer, affect all over the plate and often lead to the plate slipping off the skin at the edge, since all the stress ends up here. In a wafer according to the invention, the stress will mostly stay in the adhesive zone around the stoma, or will be taken up in the non-adhesive void volume, leaving the adhesive zone carrying the coupling ring less exposed to stress. This will enhance the wearing time and provide a more pleasant feeling.

The coupling or attachment to a collection bag may preferably be to the backing layer over the second, outer zone or to the backing layer over the void volume.

The void volume may also serve as a disconnection in the fluid flow in or under the dressing, e.g. in the case of canals of leakage fluids are being created, these will be stopped by the volume, and the fluid will be spread along the volume.

DETAILED DESCRIPTION OF THE DRAWINGS

Figure 1A:
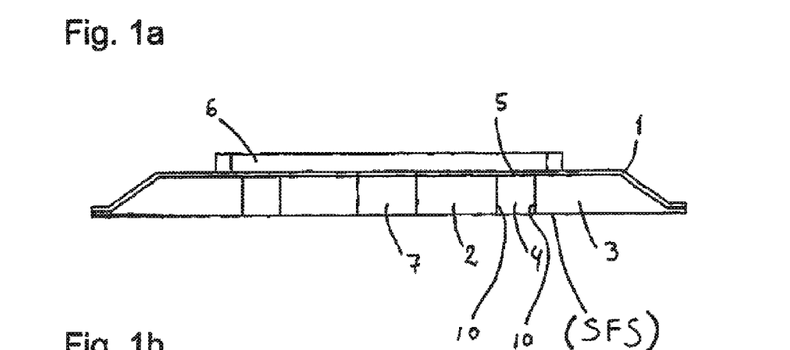
FIGS. 1a and 1b show an embodiment of the invention.

In Figure 1a is shown an embodiment of the invention in cross-section. The wafer comprises a backing layer (1) and a layer of adhesive that has on a skin-facing surface (SFS) a first and a second adhesive zone (2, 3), the zones being separated by a void volume (4). The shown embodiment is a wafer for an ostomy appliance, and comprises further coupling means (6) for attaching a collecting bag (not shown) attached to the non-skin-facing surface of the backing layer and the wafer is further provided with an aperture (7) for accommodating a stoma. The void volume (4) is defined by the backing layer (5) over the volume, the edge portions of the adhesive (10) and the skin-facing surface (SFS) and constitutes a canal, where the backing layer (5) is not in contact with the skin.

Figure 1B:
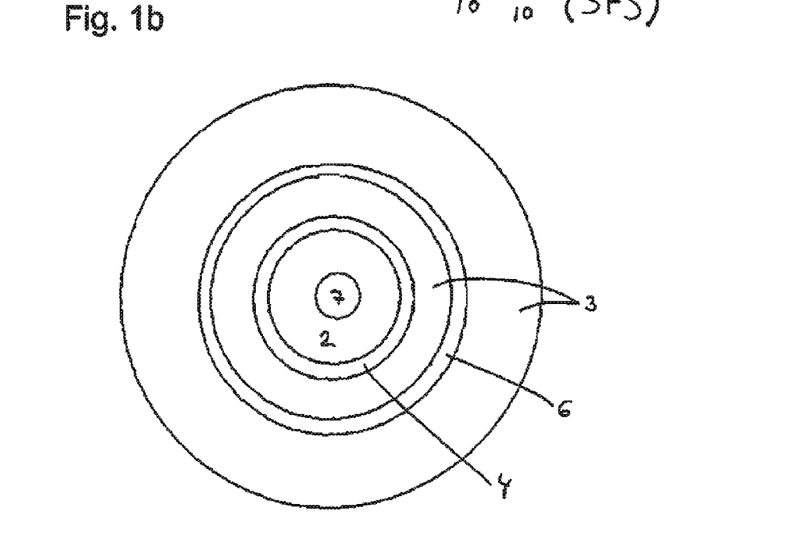

The same embodiment of the invention is shown in a top view in FIG. 1b. The adhesive zones (2, 3) are in the form of concentric circles, separated by the void volume (4).

Figure 2A:
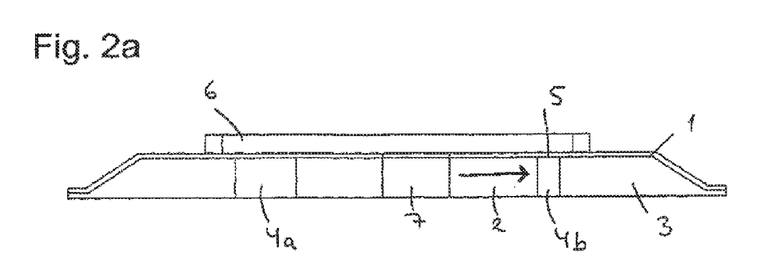
FIGs. 2a and 2b show the same embodiment of the invention exposed to lateral forces.
Figure 2B:
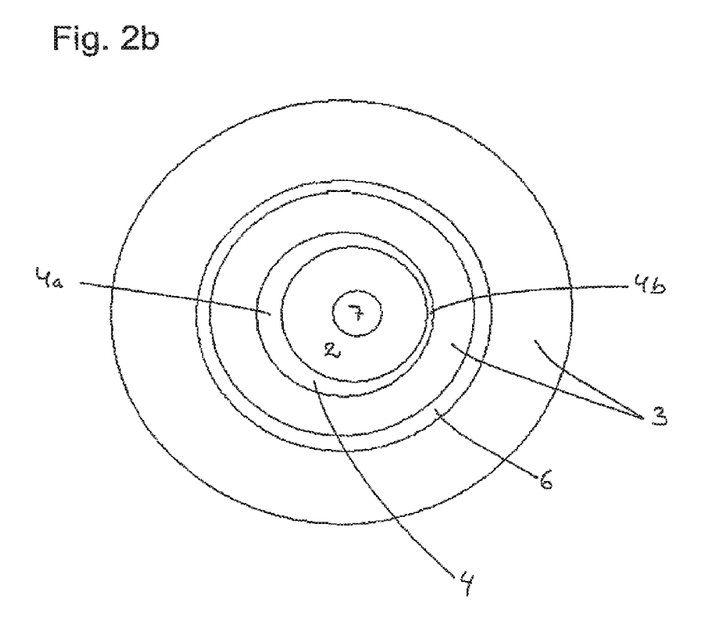

As shown in FIG. 2a, the void volume is able to uptake lateral movements of the first adhesive zone (2) with respect to the second adhesive zone (3). Here the first adhesive zone is displaced laterally to the right (shown by arrow), e.g. by the movements in the skin of the patient, or by unintended pull in the collection bag. The right side of the void volume (4a) is compressed to a smaller width and the left side of the volume (4b) is broadened and the backing layer (5) over the volume is stretched. The situation is illustrated from a top view in FIG. 2b.

Figure 3A:
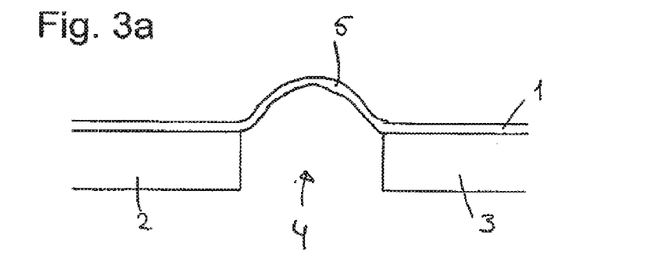
FIGS. 3a-d shows a detailed view of embodiments of the invention and
FIGS. 4a and 4b shows a detailed view of embodiments of the invention.
Figure 3B:
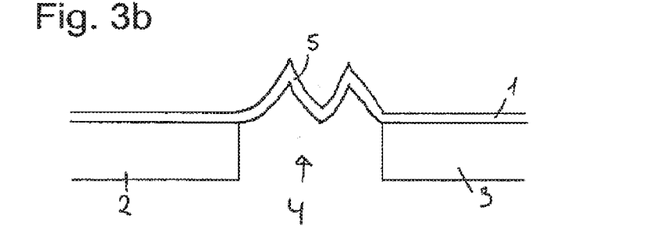
Figure 3C:
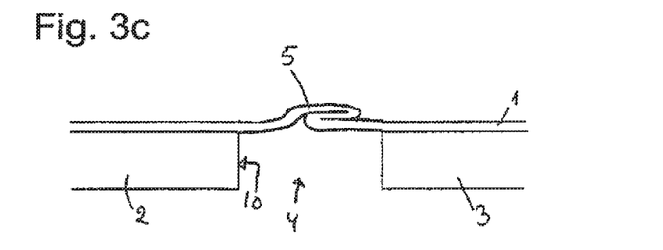
Figure 3D:
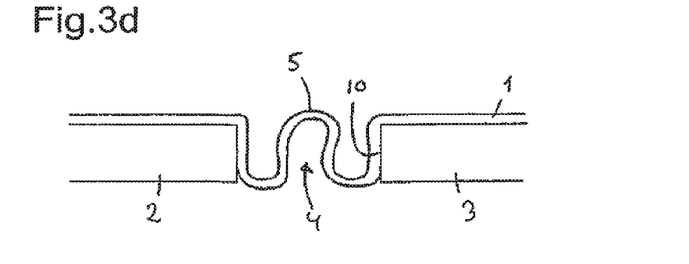

In order to enhance the flexibility of the wafer, the backing layer over the void volume may be deformed to provide excess of material. Different embodiments of the invention with deformed backing film are shown in FIGS. 3a-3d. In FIG. 3a the backing layer (5) has been deformed into a bulge, providing excess material for providing enhanced lateral movement. In FIGS. 3b and 3c, the backing layer (5) has been deformed and plied into vertical pleats (FIG. 3b) and lateral pleats (FIG. 3c). FIG. 3d shows an embodiment of the invention wherein the backing layer (5) has been deformed and brought in contact with the edge portions of the adhesive zones. Excessive material is in the form of a bulge that may serve as a canal.

Figure 4A:
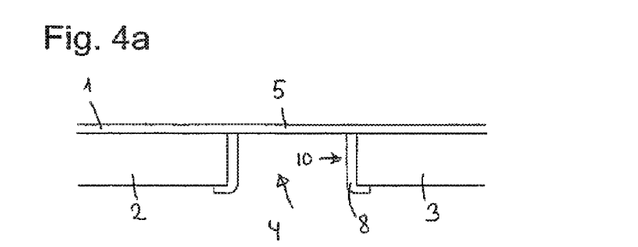
Figure 4B:
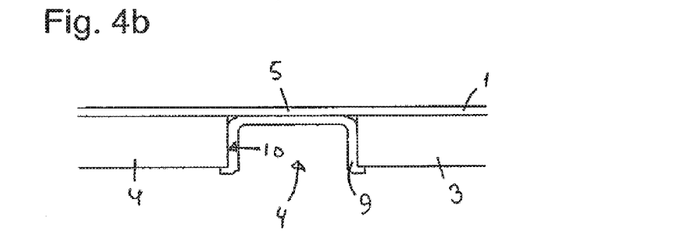

FIGS. 4a and 4b show detailed views of the void volume (4), where the edge portions (10) of the adhesive zones (2, 3) are coated in order to make them non-adhesive. In FIG. 4a, the edge portions (10) have been coated by a non-adhesive layer (8). The non-adhesive layer may cover both opposite edge portions (10), or only one of the edge portions may be covered. If only one edge portion is covered, the non-adhesive layer (8) may preferably show non-stick properties with regard to the adhesive of the non-covered edge portion. The non-adhesive layer (8) may only cover the edge portions or it may, as shown on FIG. 4a, extend to cover the edge portion of the adhesive surface too. The non-adhesive layer (8) may be in the form of a film or a coating.

FIG. 4b shows an embodiment wherein a non-adhesive layer (9) is extending over all three walls (10, 5). If the backing layer (5) over the void volume has been deformed, the non-adhesive layer (9) is following the configuration of this. The non-adhesive layer (9) should show at least the same elastic/plastic properties as the backing film (5), in order not to disturb the flexibility of this.

Figure 5:
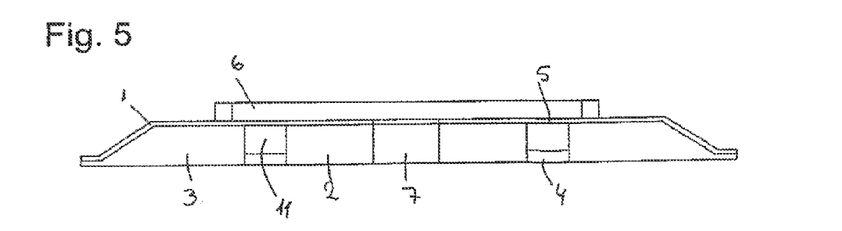
FIG. 5 shows an embodiment of the invention.

FIG. 5 shows an embodiment of the invention wherein the void volume (4) comprises a foam (11). The foam (11) may have approximately the same volume as the void volume (4), as shown in FIG. 5, or the foam (11) may have a smaller volume. The foam (11) may prevent the adhesive edges (10) from sticking together and it may help control leakage of fluid. The foam (11) is soft and easily compressible in order not to inhibit the movements of the adhesive zones relative to each other.

Figure 6:
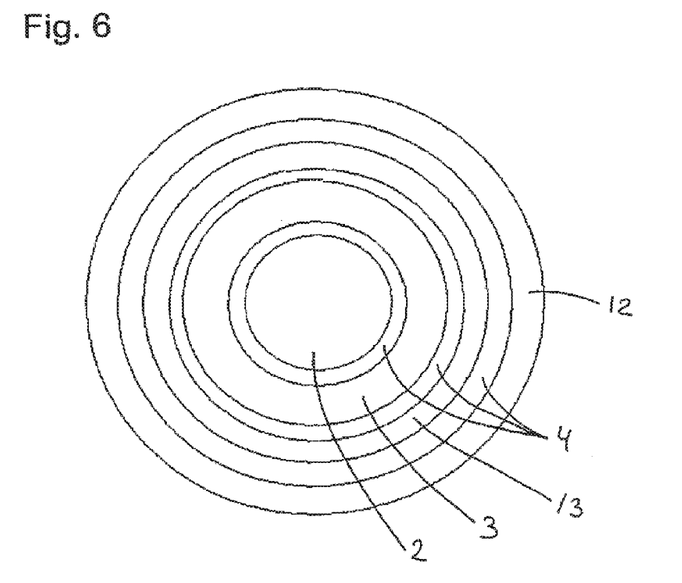
FIG. 6 shows an embodiment of the invention.

In FIG. 6 is shown an embodiment of the invention wherein the wafer comprises multiple adhesive zones (2, 3, 12, 13) separated by void volumes (4).

Figure 7:
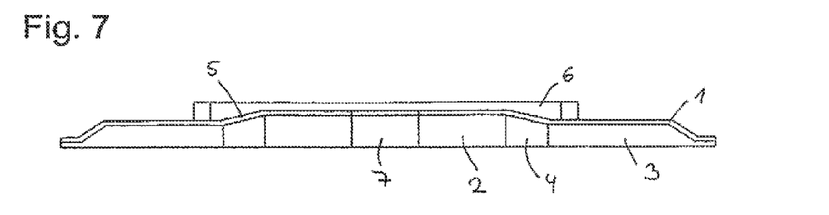
FIG. 7 shows an embodiment of the invention and
FIG. 8 shows and embodiment of the invention.

FIG. 7 shows an embodiment of the invention wherein the first central adhesive zone (2) is thicker than the second peripheral adhesive zone (3).

Figure 8:
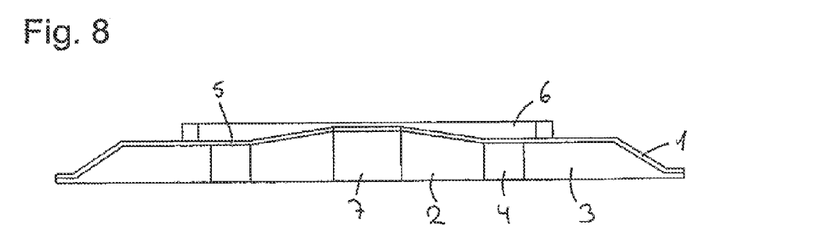

FIG. 8 shows an embodiment wherein the first adhesive zone (2) is thicker at the part surrounding the aperture (7) for the stoma than at the portion closest to the second adhesive zone (3). The increasing thickness of the adhesive is shown in the figure as a linear slope, but the slope may also be rounded, e.g. grow exponentially towards the centre.

FIG. 9 illustrates the void volume 4 is provided with moisture indicator means 15. Such indicator means may e.g. be in the form of a colour indicator producing a change of colour when exposed to moisture. Thus it will be easy for the user or care personnel to see that it is time for changing the wafer.

The invention claimed is:

1. An adhesive wafer configured for use with an ostomy faceplate, the adhesive wafer comprising:
a backing layer attached to a first surface of a layer of adhesive, said layer of adhesive having a second surface configured for adhesion to skin, said layer of adhesive comprising a first adhesive zone separated from a second adhesive zone by a void volume, said void volume being defined by the backing layer on one surface and further defined on sides by an edge of each of the first and the second adhesive zones extending between the first and second surfaces of the adhesive, and wherein the first and the second adhesive zones are adapted to move independently of each other with respect to a lateral plane of the backing layer.

2. An adhesive wafer according to claim 1 wherein the backing layer is non-adhesive.

3. An adhesive wafer according to claim 1, wherein the backing layer is stretchable.

4. An adhesive wafer according to claim 1, wherein the backing layer is plied.

5. An adhesive wafer according to claim 1, wherein the second adhesive zone surrounds the first adhesive zone.

6. An adhesive wafer according to claim 1, wherein the first and the second adhesive zones comprise different adhesives.

7. An adhesive wafer according to claim 1 wherein the wafer comprises a coupling ring.

8. An adhesive wafer according to claim 1 wherein the void volume comprises a foam absorbent pad disposed in a portion of the void volume.

9. An adhesive wafer according to claim 1 wherein the void volume comprises a foam disposed in a portion of the void volume.

10. An adhesive wafer according to claim 1 wherein a lateral width of the void volume is 1-10 mm.

11. An adhesive wafer according to claim 1 wherein a thickness of the layer of adhesive is 0.2-2 mm.

12. An adhesive wafer according to claim 1 wherein a thickness of the first adhesive zone is different from a thickness of the second adhesive zone.

13. An adhesive wafer according to claim 1 wherein the first adhesive zone has a varying thickness that is thickest at a central portion.

14. An adhesive wafer according to claim 1 wherein the edge of each of the first and the second adhesive zones is provided with a non-adhesive layer.

15. An adhesive wafer according to claim 14 wherein the non-adhesive layer is in the form of a coating.

16. An adhesive wafer according to claim 14 wherein the non-adhesive layer is in the form of a polymer film.

17. An adhesive wafer according to claim 14 wherein the non-adhesive layer covers the backing layer.

18. An adhesive wafer according to claim 1 wherein the void volume is provided with moisture indicator means.

* * * * *